US00PP11644P

United States Patent [19]

Noodelijk

[11] Patent Number: Plant 11,644

[45] Date of Patent: Nov. 21, 2000

[54] CHRYSANTHEMUM NAMED 'REMCO YELLOW'

[75] Inventor: Robert Noodelijk, Woubrugge, Netherlands

[73] Assignee: Chrysanthemum Breeders Association N.V., Netherlands

[21] Appl. No.: 09/149,461

[22] Filed: Sep. 9, 1998

[51] Int. Cl.[7] ..... A01H 5/00

[52] U.S. Cl. ..... Plt./295

[58] Field of Search ..... Plt./286, 295, 296

*Primary Examiner*—Howard J. Locker

[57] ABSTRACT

A new and distinct cultivar of chrysanthemum plant named Remco Yellow, bearing medium sized blooms with yellow ray florets and a greyed-orange center and performance of 21 days.

2 Drawing Sheets

The present plant is related to the plant in the following co-pending application:

| application Ser. No. | Filing Date | Title |
|---|---|---|
| 09/149,459 | 9/9/98 | Remco |

BACKGROUND OF THE INVENTION

The present invention comprises a new and distinct cultivar of chrysanthemum plant which is a natural occurring sport of a parent chrysanthemum named Remco. Patent chrysanthemum Remco is also described in this application. The new cultivar was discovered as a whole plant mutation in 1993 by R. Noodelijk in a controlled environment (greenhouse) in Ter Aar, Holland. The first act of asexual reproduction of Remco Yellow was accomplished when vegetative cuttings were taken from the initial selection in Aug. 1993 in Ter Aar, Holland.

SUMMARY OF THE INVENTION

The present invention is a new and distinct variety of chrysanthemum bearing medium sized blooms with yellow ray florets and a greyed-red center.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
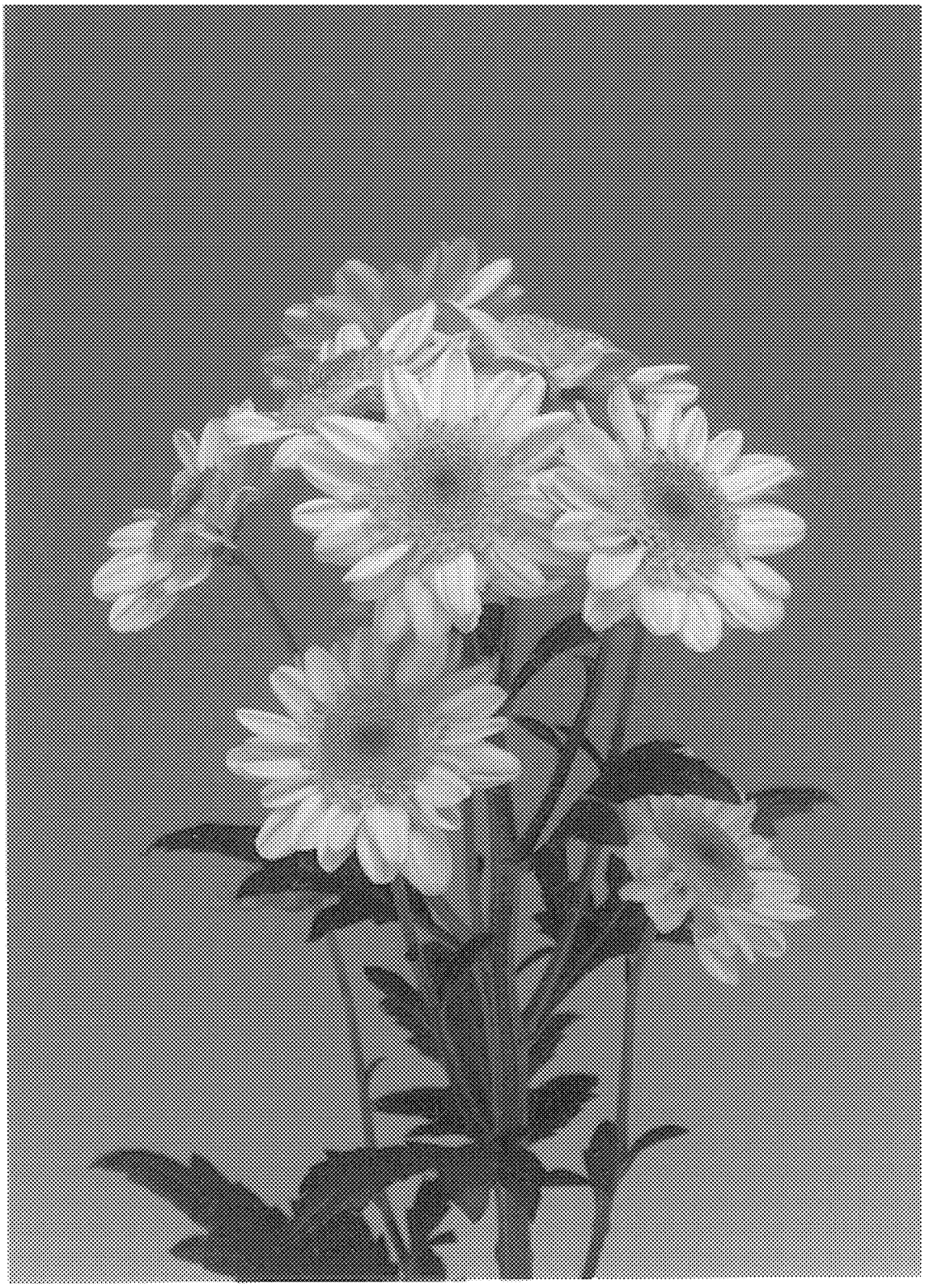
FIG. 1 shows the stem of the cultivar in full bloom.
Figure 2:
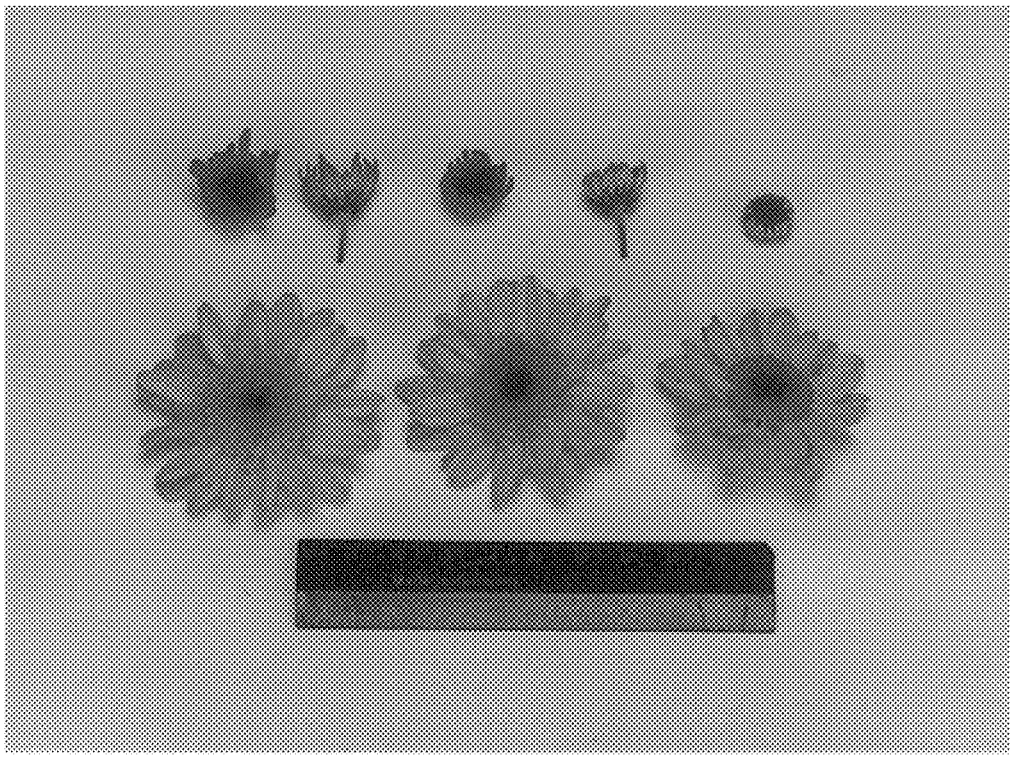
FIG. 2 shows the various stages of bloom of the new cultivar.
Figure 3:
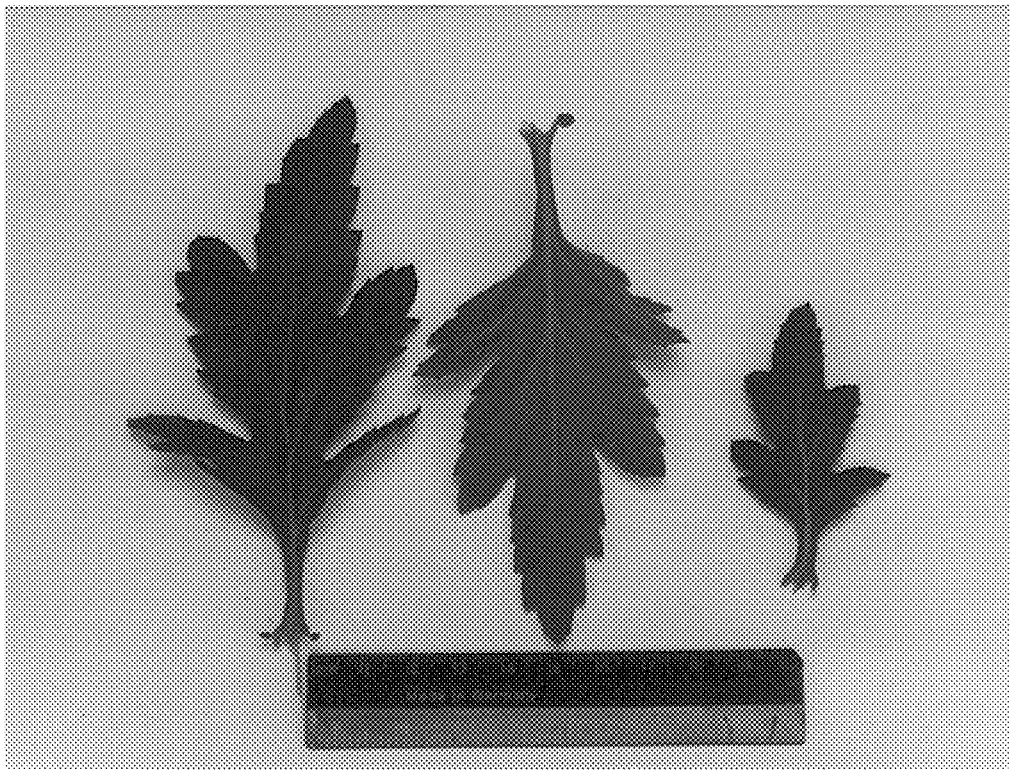
FIG. 3 shows the foliage and petiole of the new cultivar.

This new variety of chrysanthemum is of the botanical classification *Dendranthema grandiflora*. When grown in the vicinity of Ter Aar, Holland, it has a response time of approximately 8 weeks. This new variety produces medium sized blooms with yellow ray florets and a greyed-red center having a 3 week performance (i.e., vase life of 21 days). This new variety of chrysanthemum has been found to retain its distinctive characteristics throughout successive propagations. However, the phenotype may vary significantly with variations in environment such as light intensity and temperature. To show the phenotype as described Remco Yellow may be planted under greenhouse conditions in Holland without assimilation lightning between week 2 and 40. With assimilation lightning (minimum level 2500 lux) Remco Yellow may be planted year round under greenhouse conditions in Holland.

The following is a discription of the plant and characteristics (color designations are from the R.H.S. Colour Chart) that distinguish it from related known varieties and its antecedents:

The color designations are taken from the plant itself. Accordingly, any discrepancies between the color designations and the colors depicted in the photographs are due to photographic tolerances.

Botanical Description of Remco Yellow and Remco

| CULTIVAR | REMCO YELLOW | Parent Cultivar REMCO |
|---|---|---|
| Bud | | |
| Size | Large cross section ±1.5 cm height ±1.2 cm | large cross section ±1.5 cm height ±1.2 cm |
| Outside Color | yellow-orange 21A to red 46A at the tip | mainly red 49 D, red-purple 64 D at the tip |
| Bloom | | |
| Size | medium | medium |
| Fully Expanded | 6–6½ cm | 6–6½ cm |
| Borne | upper portion single flower per peduncle, lower portion plural flower per peduncle | upper portion single flower per peduncle, lower portion plural flower per peduncle |
| Number of Blooms per single stem | average of 11 | average of 11 |
| Peduncle Lengths | Near the top ±12 cm, near the middle ±26 cm, near the bottom ±28 cm. | Near the top ±12 cm, near the middle ±26 cm, near the bottom ±28 cm. |
| Peduncle Lateral Shoot, Attachment | weak to medium | medium |
| Peduncle Lateral Shoot, Angle | 35°–30° | 40° |
| Form | semi-double (anemone) | semi-double (anemone) |
| Performance (lastingness of the total inflorescence) | good 21 days (18°–20° C.) | good 21 days (18°–20° C.) |
| Color | | |
| Center of Flower/ Disc floret | Greyed-orange 170 A with a dot in the very center of greyed-red 178 C | Between orange-red 33 B and 34 A with a dot in the very center of red 53 B |

-continued

Botanical Description of Remco Yellow and Remco

| CULTIVAR | REMCO YELLOW | Parent Cultivar REMCO |
|---|---|---|
| Color of the upper surface of the majority of the ray-florets | Yellow-orange 16 A | red-purple 69C but slightly more white |
| Color of the lower surface of the majority of the ray-florets. | yellow 10C with greyed-red 182D between the ribs | red-purple 69B but slightly paler |
| Tonality from Distance | a yellow anemone type flower with a red teint and a greyed-orange cushion | a pinkish white anemone type flower with an orange-red cushion |
| Discoloration | ray-florets to yellow-orange 16 C, cushion to yellow 13A with greyed-red 178A at the tips | ray-florets to almost white, center (cushion) to orange-red 34 C |
| Pollen | (not present) | (not present) |
| Ray florets | | |
| Texture | upper side smooth, underside smooth | upperside smooth, underside smooth |
| Number | 25–30 (two rows) | 25–30 (two rows) |
| Cross-section | convex, two keels | convex, no keels |
| Longitudinal axis of majority | straight | reflexing |
| Shape of tip | rounded | dentate |
| Fragrance | typical chrysanthemum | typical chrysanthemum |
| Disc Diameter | large to very large (2.5–3.0 cm) | large to very large (2.5–3.0 cm) |
| Reproductive Organs | | |
| Stamen (present in disc florets only) | yellow-green, thick ±5 mm in length | yellow-green, thick ±5 mm in length |
| Pollen | (not present) | (not present) |
| Styles (present in disc and ray florets) | green, thick | green, thick |
| Style Length | ±7 mm | ±7 mm |
| Stigmas | yellow-green | yellow-green |
| Stigma Width | ±3 mm | ±3 mm |
| Ovaries | enclosed in calyx | enclosed in calyx |
| Plant | | |
| Form | spray mum meant for erect culture Herbaceous | spray mum meant for erect culture Herbaceous |

-continued

Botanical Description of Remco Yellow and Remco

| CULTIVAR | REMCO YELLOW | Parent Cultivar REMCO |
|---|---|---|
| Growth | medium | medium |
| Height | ±110–120 cm | ±110–120 cm |
| Stem Color | green 146A | green 139A |
| Stem Strength | medium to strong | medium to strong |
| Stem Brittleness | present | absent |
| Stem Anthocyanin Coloration | present (mainly at the base) | present (mainly at the base) |
| Internodes | medium (2.5–3.0 cm) | medium (2.5–3.0 cm) |
| Flowering Response (photoperiodic controlled crop, no natural growing) | 8 weeks | 8 weeks |
| Foliage | | |
| Color | upper side between 137A and yellow-green 147A, underside near green 137B | upper side between 137A and yellow-green 147A, underside near green 137B |
| Size | length ±12 cm, width ±6 cm | length ±12 cm, width ±6 cm |
| Quantity (per single stem) | 22–26 | 22–26 |
| Shape | lobed | lobed |
| Texture | fleshy | fleshy |
| Ribs and Veins | ribs well developed, veins not so developed | ribs well developed, veins not so developed |
| Edge | crenated | crenated |
| Shape of Base of Sinus Between Lateral Lobes | round | round |
| Margin of Sinus Between Lateral Lobes | converging | converging |
| Shape of Base | uneven | uneven |
| Apex | cuspidate | cuspidate |
| Year of Discovery | 1993 | 1992 |

I claim:

1. A new and distinct variety of chrysanthemum plant as described and illustrated.

* * * * *